(12) United States Patent
Parsons et al.

(10) Patent No.: US 8,193,104 B2
(45) Date of Patent: Jun. 5, 2012

(54) CROSSLINKABLE CATIONIC EMULSION BINDERS AND THEIR USE AS A BINDER FOR NONWOVENS

(75) Inventors: John C. Parsons, Easton, PA (US); James L. Walker, Whitehouse Station, NJ (US); Christopher Barcomb, Somerset, NJ (US)

(73) Assignee: Celanese International Corporation, Dallas, TX (US)

( * ) Notice: Subject to any disclaimer, the term of this patent is extended or adjusted under 35 U.S.C. 154(b) by 1781 days.

(21) Appl. No.: 10/496,546

(22) PCT Filed: Nov. 25, 2002

(86) PCT No.: PCT/US02/37932
§ 371 (c)(1),
(2), (4) Date: May 5, 2005

(87) PCT Pub. No.: WO03/048441
PCT Pub. Date: Jun. 12, 2003

(65) Prior Publication Data
US 2005/0239356 A1 Oct. 27, 2005

(51) Int. Cl.
*B32B 3/00* (2006.01)
*B32B 5/02* (2006.01)
*B32B 9/04* (2006.01)
*B32B 27/30* (2006.01)
*B29C 65/00* (2006.01)
*C08F 2/16* (2006.01)

(52) U.S. Cl. .......... 442/59; 442/154; 442/155; 442/173; 442/174; 156/60; 524/459

(58) Field of Classification Search ............... 442/59, 442/152–155, 164–174; 156/60
See application file for complete search history.

(56) References Cited

U.S. PATENT DOCUMENTS

| | | | |
|---|---|---|---|
| 2,702,780 A | 2/1955 | Lerner | 167/84 |
| 3,283,358 A | 11/1966 | Merriam | 16/20 |
| 3,926,890 A | 12/1975 | Huang et al. | 260/29.6 H |
| 4,012,253 A | 3/1977 | Gange | 96/1.5 |
| 4,151,148 A | 4/1979 | Chasin et al. | 260/29.6 RB |
| 4,308,189 A * | 12/1981 | Moritani et al. | 524/459 |
| 4,692,374 A | 9/1987 | Bouchette | 428/288 |
| 4,946,617 A | 8/1990 | Sheridan et al. | 252/91 |
| 4,987,632 A | 1/1991 | Rowe et al. | 15/104.93 |
| 5,200,037 A | 4/1993 | Noda | 162/168.2 |
| 5,252,663 A * | 10/1993 | Chandran et al. | 524/813 |
| 5,972,001 A | 10/1999 | Yoon | 606/139 |
| 6,667,290 B2 | 12/2003 | Svendsen | 510/438 |
| 2003/0008591 A1 * | 1/2003 | Parsons et al. | 442/414 |

FOREIGN PATENT DOCUMENTS
WO WO 02/48296 A2 6/2002

* cited by examiner

*Primary Examiner* — Lynda Salvatore
(74) *Attorney, Agent, or Firm* — Michael W. Ferrell

(57) ABSTRACT

The present invention is directed to a cationic polymer emulsion binder that may be combined with a cationic active ingredient and used as a non-woven binder. This combination of cationic binder and cationic active ingredient may occur as a mixture of a cationic binder and at least one cationic active ingredient, which is then applied to loose fibers to form a non-woven; or the combination may occur after a non-woven is formed using a cationic binder, and said non-woven is then contacted with a cationic active ingredient. Non-woven wipes of the invention retain far less cationic active ingredients during use, resulting in less waste and less use of the active ingredients for the same effect as wipes made with anionic or non-ionic binders.

17 Claims, No Drawings

CROSSLINKABLE CATIONIC EMULSION BINDERS AND THEIR USE AS A BINDER FOR NONWOVENS

FIELD OF THE INVENTION

The present invention relates to a crosslinkable cationic polymer emulsion binder that may be used as a non-woven binder. The binder may be combined with a cationic active ingredient. This combination of cationic binder and cationic active ingredient may occur as a mixture of a cationic binder and at least one cationic active ingredient, which is then applied to loose fibers to form a non-woven; or the combination may occur after a non-woven is formed using a cationic binder, and said non-woven is then contacted with a cationic active ingredient.

BACKGROUND OF THE INVENTION

Non-woven materials consist of a loosely assembled mass of fibers that are bound together with a polymeric binder to form a self-sustaining web that can be used to produce consumer towels, disposable wipes, and other such articles. Generally anionic binders, and to a lesser extent non-ionic binders, are used to produce the non-woven articles.

Non-woven materials are particularly useful for the production of disposable wipes. Disposable wipes are used to adsorb spills, and are also used to apply solutions containing active ingredients to surfaces. Surfaces to which the solutions can be applied range from a hard surface, such as a floor, countertop or table, to a soft surface such as skin. Active ingredients may be harsh cleaning and disinfecting chemicals, or may be skin moisturizers. Wipes used to apply active ingredients may be dry wipes that must be contacted with a solution containing an active ingredient, or may be pre-moistened with one or more active ingredients.

Many useful active ingredients are cationic. Cationic active ingredients are attracted to anionic binders typically used to produce wipes. Once a cationic ingredient is attached to an anionic binder, it is difficult to release the active ingredient onto the surface. As a result, as much as half or more of the active ingredients remain attached to the wipe and are disposed of, instead of accomplishing their intended purpose. This results in the waste of costly active ingredients.

Cationic emulsion polymers are known in the art, and have been produced by either a) co-polymerizing a cationic monomer (or a monomer which can be hydrolyzed to give a cationic character) with non-ionic monomers, or b) by forming an emulsion polymer using cationic stabilizers or surfactants.

U.S. Pat. No. 4,308,189 discloses a cationic polymer emulsion in which ethylenically unsaturated monomers are polymerized in the presence of cationically-modified poly(vinyl alcohol) as the stabilizer. The cationic polymer exhibited high adhesive affinity for substances tending to be negatively charged, including as a paper strength additive or a non-woven binder. U.S. Pat. No. 5,591,799 discloses an emulsion copolymer containing N-vinyl formamide units, and in particular vinyl acetate polymers or ethylene-vinyl acetate copolymers containing cationic amine functionality.

U.S. Pat. No. 5,895,557 discloses a saturated paper for ink jet printing having either a nonionic or cationic latex binder, plus a cationic polymer which is not a binder. The use of a non-ionic binder is preferred, and no cationic binder compositions are provided in the specification or examples. No disclosure is made of application to non-wovens.

U.S. Pat. No. 5,540,987 discloses a crosslinkable emulsion non-woven binder containing N-methylol acrylamide as a crosslinking monomer. It is disclosed that the emulsion may be made with anionic, cationic or nonionic surfactants, however only anionic and non-ionic surfactants are exemplified.

There is a need for a non-woven material, made with a cationic binder for use as a wipe with cationic active ingredients. The cationic binder needs to have a combination of good absorbency, good hand, good release properties of cationic active ingredients, and good strength.

Surprisingly it has been found that crosslinkable cationic emulsion polymers can be used as binders for non-woven materials, providing good wet and dry tensile strength, good hand, and good release properties for cationic active ingredients.

SUMMARY OF THE INVENTION

The present invention is directed to a polymeric binder composition comprising a crosslinkable cationic emulsion polymer. The polymeric binder can be used as a binder in the production of a non-woven material. The polymeric binder can be combined with one or more cationic active ingredients, either prior to or following application of the binder to a non-woven web.

Further, the invention is directed to a method for applying a cationic active ingredient to a surface comprising:
 a) contacting a solution comprising a cationic active ingredient with a non-woven material, said non-woven material comprising a crosslinkable cationic emulsion polymer;
 b) spreading the cationic active ingredient solution on a surface by moving said non-woven material on said surface.

DETAILED DESCRIPTION OF THE INVENTION

The present invention is directed to a crosslinkable cationic polymer emulsion binder that may be used as a non-woven binder. The binder may be combined with a cationic active ingredient. This combination may occur as a mixture of a cationic binder and at least one cationic active ingredient, which is then applied to loose fibers to form a non-woven; or the combination may occur after a non-woven is formed using a cationic binder, and said non-woven is then contacted with a cationic active ingredient.

By "crosslinkable" as used herein is meant a polymer that is capable of undergoing crosslinking, either by a self-crosslinking mechanism, or by the incorporation of a functional monomer into the polymer backbone which can undergo a post-polymerization crosslinking reaction to form crosslinks.

Examples of monomers which can be incorporated into the polymer backbone to provide self-crosslinking include N-methylolacrylamide, N-methylol methyacrylamide, N-methylol allyl carbamate, iso-butoxy methyl acrylamide, n-butoxy methyl acrylamide, and mixtures thereof. The polymer can also be crosslinkable by means of incorporating a functional monomer into the polymer. Functional monomers include those containing functional groups such as hydroxyl, carboxyl, and amide. These functional monomers can be cross-linked following polymerization by means known in the art. Examples of functional monomers include, but are not limited to acrylic acid, methacrylic acid, maleic acid, maleic anhydride, hydroxyethylacrylate, hydroxybutylacrylate, hydroxypropylacrylate, hydroxyethylmethacrylate, hydroxybutylmethacrylate, hydroxypropylmethacrylate The functional monomer is present at from 0 to 10 percent by weight, and preferably from 3 to 5 percent by weight, based on the total amount of monomer.

Cationic binders useful in the present invention are produced either by the incorporation of a cationic monomer into the polymer backbone, by the use of a cationic surfactant or stabilizer in the polymerization, or a combination of the two. Cationic polymers can be formed by copolymerizing at least one ethylenically unsaturated cationic monomer with at least one other ethylenically unsaturated monomer. Examples of cationic monomers useful in the present invention include, but are not limited to, dimethyl amino ethyl acrylate or methacrylate, tertiary butyl amino ethyl acrylate, N-(1,1-dimethyl-3-dimethylaminopropyl)acrylamide, trimeth2yl-3-(1-acrylamido-1,1-dimethylpropyl)ammonium chloride, N-(1,1-dimetyl-3-dimethylaminobutyl)acrylamide, trimethyl-3-(1-acrylamido-1,1-dimethylbutyl)ammonium chloride, N-(1-methyl-1,3-diphenyl-3-diethyl-aminopropyl) methacrylamide, n-(3-dimethyl-amino-propyl)acrylamide, trimethyl-3-(1-acryl -amidopropyl)ammonium chloride, dimethylacryl-amidopropyl-4-trimethylammoniumbutenyl-2-ammonium chloride, 2-acrylamidomethoxy)ethyltrimethylammonium chloride, N-(3-dimethyl-aminopropyl) methacrylamide, trimethyl-3-(1-methacrylamidopropyl) ammonium chloride. The level of cationic monomer can range from 0 to 25 parts per hundred monomer (pphm), preferably from 0.1 to 20 pphm, and most preferably from 0.5 to 10 pphm. The polymer is formed by a free radical emulsion polymerization, by means known in the art. The other (non-cationic) monomer(s) may be selected from any monomer capable of undergoing free radical polymerization, as known in the art, including but not limited to, (meth)acrylates, maleates, (meth)acrylamides, vinyl esters, itaconates, styrenics, unsaturated hydrocarbons and acrylonitrile, nitrogen functional monomers, vinyl esters, alcohol functional monomers, unsaturated hydrocarbons, and (meth)acrylates. Preferred non-cationic monomers include ethylene-vinyl acetate, and vinyl acetate-acrylate Monomers having an anionic character are undesirable in polymers of the present invention.

Cationic polymers can also be produced by a standard emulsion polymerization using at least one cationic surfactant or stabilizer. Examples of useful cationic surfactants include, but are not limited to, alkyl quaternary ammonium salts and alkyl quaternary phosphonium salts such as: alkyl trimethyl ammonium chloride, dieicosyldimethyl ammonium chloride; didocosyldimethyl ammonium chloride; dioctadecyldimethyl ammonium chloride; dioctadecyidimethyl ammonium methosulphate; ditetradecyldimethyl ammonium chloride and naturally occurring mixtures of above fatty groups, e.g. di(hydrogenated tallow)dimethyl ammonium chloride; di(hydrogenated tallow)dimethyl ammonium methosulphate; ditallow dimethyl ammonium chloride; and dioleyidimethyl ammonium chloride. Examples of useful stabilizers include, but are not limited to cationically modified poly(vinyl alcohol), cationically modified starch. Preferred cationic surfactants and stabilizers include alkyl trimethyl ammonium chlorides, with the most preferred being cetyl trimethyl ammonium chloride and lauryl trimethyl ammonium chloride. The cationic stabilizer or surfactant is generally used in an amount of from 0.25 to 10 percent by weight, based on the total amount of monomer, and preferably from 0.4 to 5 percent by weight. The cationic stabilizer or surfactant may be used in combination with nonionic surfactants or stabilizers. The surfactant or stabilizer is generally added to the initial charge to the reactor, but some may be delay-fed into the reactor along with a monomer and initiator charge.

The polymers of the present invention have a Tg in the range of from −60° C. to +105° C., and preferably from −40° C. to +35° C.

The cationic binder is first applied to the non-woven fibers, then dried, prior to contact with the cationic active ingredient(s).

The fibers can be natural or synthetic and are formed by means known in the art, such as air-laid, dry-laid, and wet-laid.

The binder is applied to the fiber by any means known in the art, such as print, foam, saturate, coating and spraying, then dried on steam cans or ovens as currently practiced in the production of non-woven rolled goods.

Binder add-on levels for non-wovens useful in the present invention can be from 0.1 to 100 percent, preferably from 3 to 30 percent. Non-wovens made with the cationic binder of the present invention are useful in applications known in the art, such as wipes, diapers, feminine hygiene products, and filtration.

One or more cationic active ingredients may be combined with the cationic binder, either before or after the binder is applied to the non-woven web. The cationic active ingredients are present at a level to be effective in which they form an effective amount in the final use application. Cationic active ingredients typically used with non-woven wipes include, but are not limited to benzalkonium chlorides, benzethonium chlorides, and typical quaternary alkyl ammonium chloride actives. When the active ingredient(s) are mixed with the emulsion binder prior to being applied to the non-woven fibers, the ratio of the active ingredient(s) to the non-woven binder is generally from 0.10 to 5 percent based on the binder solids, and preferably from 1 to 2 percent.

Generally the cationic active ingredients are applied to the non-woven web following the application and drying of the cationic binder. The active ingredients may be made into a solution, with an aqueous solution preferred. The solution may be applied to the non-woven material by means of spray or saturation. The treated non-woven may be dried, stored wet, or used as soon as contacted with the solution containing the cationic active(s).

Other anionic, nonionic, and cationic active ingredients may be added to the cationic binder, either before or after the binder is applied to the non-woven web, to exhibit superior compatibility and/or efficacy versus anionic or nonionic binders.

Typical scenarios include: non-woven wipes saturated with a solution containing the cationic active ingredient(s) and stored and dispensed in the moist condition until use; a wipe dipped into a solution containing cationic active ingredient(s), then used to wipe a surface; a solution containing cationic active ingredients sprayed onto a surface, then spread using a dry wipe bound with a cationic binder.

Cationic active ingredients may be applied to a surface by means of non-wovens formed with cationic binders. The advantage of this method is that much less of the cationic active ingredient(s) remain attached to the cationic binder than to a typical anionic non-woven binder, thus more active ingredient is applied to the surface, and less remains on the non-woven and is disposed of. This allows one to apply less of the active ingredient to the non-woven, and still have the same level of active ingredient applied to the surface—saving active ingredient costs. Surfaces to which the cationic active ingredient may be applied include, but are not limited to skin, hair, floors, counters, furniture, dishes, bathroom fixtures, automotive finishes and painted surfaces.

Non-woven materials formed with the cationic binder of the present invention may exhibit an anti-microbial action, even without additional additives, since many of the quaternary amine monomers and surfactants used to produce the cationic binder are known to exhibit some anti-microbial action. This low level of anti-microbial action can reduce odors associated with microbe growth in non-wovens exposed to moisture.

In addition to being useful as a non-woven binder, the crosslinkable cationic emulsion of the present invention may also be used in the production and coating of paper. The cationic emulsion may be applied in the wet-end section of the fiber deposition process in paper production. The cationic emulsion may be used as a paper coating and also as a paper saturant.

In addition to having excellent release properties toward cationic active ingredients, non-wovens and paper formed with the crosslinkable cationic binders of the present invention also have an affinity for anionic substances—such as clothing, dust, and pigments. The affinity of the cationic binder for the anionic non-woven fibers should result in more binder being deposited on the fibers, which leads to a lower usage and less waste of binder in the manufacturing process. The affinity of cationic non-woven materials for anionic substances is also advantageous in many applications. Wipes made with the non-wovens of the present invention are better able to attract and retain dust—for more efficient cleaning. Feminine hygiene panty liners made with the non-wovens have more affinity for clothing, allowing them to better remain in place. Many non-wovens are colored with anionic pigments, and the cationicly bound non-woven could provide for better pigment retention and result in less pigment usage during manufacture. The better retention of pigment for paper made with a cationic binder could result in more efficient printing by laser-jet and inkjet printing systems. The cationic binder will offer superior compatibility with cationic water repellents for medical non-woven applications or flame retardants for industrial and automotive non-woven applications and will offer superior retention and improved durability of these types of actives in the non-woven.

Surprisingly, it has been found that non-wovens made with the cationic binder of the present invention have a superior absorbency rate compared with the absorbency rate of non-wovens made with non-ionic binders.

The following examples are presented to further illustrate and explain the present invention and should not be taken as limiting in any regard.

EXAMPLE 1

Three self-crosslinking ethylene-vinyl acetate (EVA) co-polymer emulsions were pad saturated from a 10 percent solids formulation onto Whatman #4 Filter paper to achieve 20 percent dry binder add-on. Each of the EVA emulsions were synthesized in the same manner, except for the surfactant used to emulsify the polymer. Sample 1A is highly anionic, Sample 1B is nonionic, and Sample 1C contains cationic surfactant. All samples were formulated with 0.75% ammonium chloride (active solids on polymer solids) as a catalyst to accelerate the crosslinking reaction. The saturated papers were drum dried for 90 seconds at 210 F. and then cured for 2 minutes at 300 F. Following are the polymer performance properties that were tested. CMD, or CD refers to Cross-Machine Direction, and relates to a tensile strength pulled in a specific direction.

TABLE 1

| Polymer | 1A | 1B | 1C |
|---|---|---|---|
| Surfactant Charge | Anionic | Nonionic | Cationic |
| CMD Dry Tensile, g/in | 6190 | 5861 | 6168 |
| CMD Wet Tensile, g/in | 4126 | 4040 | 3738 |
| MEK Tensile, g/in | 4494 | 3949 | 2579 |
| Absorbency Rate, sec | 60 | 494 | 140 |
| Cobb Size, g/m$^2$ | 85 | 71 | 94 |
| Hunter "b" | 4.46 | 4.90 | 4.49 |

The cationic binder offered similar dry and wet strength as the other two binders, with vastly improved absorbancy rate.

EXAMPLE 2

Three self-crosslinking EVA co-polymers were pad saturated from a 20 percent solids formulation onto 65 grams per square meter (gsm) basis weight spun-laced rayon to achieve 20 percent dry binder add-on. The difference among the polymers is the surfactants used to emulsify the polymer. Sample 2A is highly anionic, Sample 2B is nonionic, and Sample 2C contains cationic surfactant and is based on the composition from Example 1. The saturated spunlaced rayon webs were drum dried for 90 seconds at 210 F. and then cured for 2 minutes at 300 F. The webs were spiked with 2000 ppm of benzalkonium chloride (BZK) and tested (see procedure below) for their retention/release characteristics for the benzalkonium chloride. This demonstrates that non-woven materials made with cationic binders are better at releasing cationic anti-bacterial agents onto a surface. Table 2 the results in terms of % recovered benzalkonium chloride:

Analytical Procedure for Detection of Released Benzalkonium Chloride

Procedure: 1"×3" strips of saturated spunlace non-woven were placed into a two-piece Microsep centrifugal devices in duplicate. A 0.5 mL aliquot of a 2043 ppm benzalkonium chloride (BZK) solution in water was slowly added to each wipe to saturate the fabric. A set of controls was also prepared in which the 0.5 mL aliquot of BZK was added directly to the centrifugal devices (which have a 0.45 micron nylon filter). The BZK solution was allowed to remain on the fabric for 30 minutes after which, the centrifugal devices were centrifuged at 5500 rpm for 15 minutes to express the solution from the fabric. The solution was then analyzed for BZK content by HPLC using an ion-pairing mobile phase with detection at 210 nm. For purposes of quantitation, the areas of the C-12 and C-14 BZK isomers were determined and summed together.

TABLE 2

| Polymer | 2A | 2B | 2C |
|---|---|---|---|
| Surfactant Charge | Anionic | Nonionic | Cationic |
| % Benzalkonium Chloride Recovered | 26.5% | 40.0% | 52.3% |

EXAMPLE 3

A general procedure for the preparation of a vinyl acetate-ethylene copolymer emulsion of the invention is as follows:

The initial charge to the reactor includes the following:

| | |
|---|---|
| Water (deionized) | 2100.0 g |
| Ferrous sulfate (1% aq. sol'n) | 16.0 |
| Polyvinyl alcohol (10% aq.) (88% hydrolysed) | 200.0 |
| Cetyl trimethyl ammonium chloride | 67.0 |

-continued

| | |
|---|---|
| Ethoxylated alkyl alcohol (10 EO) surfactant | 80.0 |
| Ethoxylated alkyl alcohol (30 EO) surfactant | 120.0 |
| Sodium acetate | 0.5 |
| VERSENE 100 (1%) | 16.0 |
| Phosphoric acid | 1.5 |
| Sodium Formaldehyde Sulfoxylate (SFS) | 1.6 |
| Vinyl acetate | 3200.0 g |

Ethylene - amount to equilibrate reactor to 600 psi at 50° C.

Slow additions:

| | |
|---|---|
| 1. Water | 800.0 |
| Ethoxylated alkyl alcohol (30 EO) surfactant | 40.0 |
| Sodium acetate | 1.8 |
| NMA (48%) | 417.0 |
| 2. Water (deionized) | 250.0 g |
| t-butyl hydroperoxide (70% aq.sol'n) | 16.0 |
| 3. Water (deionized) | 250.0 g |
| Sodium Formaldehyde Sulfoxylate (SFS) | 12.0 |

The pH of the initial aqueous charge was adjusted to 4.04-4.3 with the phosphoric acid. A 10 L stainless steel pressure reactor was filled with initial aqueous mix. It was flushed with nitrogen. With the agitation at about 250 rpm, the vinyl acetate was added. After closing all reactor ports, it was purged twice with nitrogen (25 to 40 psi) and then with ethylene (50 psi). It was then heated to 50° C. Agitation was increased to 550 rpm and it was pressurized with ethylene to 600 psi. The reactor temperature and ethylene pressure were allowed to equilibrate for 15-20 minutes. The ethylene supply was then closed off. Agitation was reduced to 400 rpm.

The reaction was initiated by starting both slow-additions (no. 1 and 2) at 2.5 hr. rates (80 cc/hr). After the initial temperature rise, about 2-5° C., the jacket temperature and oxidizer rate (no. 2) are adjusted to allow the temperature to reach 75° C. in about 15 minutes. The slow addition, no. 1, was started to add uniformly over 4 hrs. During the run, the oxidizer rate is adjusted to maintain a 15-20° C. average temperature delta (reaction temperature minus jacket temperature) The reaction is run until the residual vinyl acetate is reduced to 1.5-2.0%. It is then cooled to 45° C. and transferred to the degassing tank to vent off residual ethylene pressure. Defamer, Colloid 681f (Allied Colloids), was added to the degassing tank followed by finishing redo initiator. This includes 15 g of a 6% t-BHP solution, waiting 5 minutes, then 15 g of a 6% Ascorbic acid solution added over 15 minutes. This reduces the vinyl acetate to <0.2%. After cooling to 30° C., the pH is adjusted to 4-5 with 14% ammonium hydroxide. The emulsion had the final properties:

| | |
|---|---|
| Solids, % | 54.6 |
| Viscosity (20 rpm, RVT#3) | 68 cps |
| pH | 4.4 |
| % grit (200 mesh) | 0.010 |
| Tg, ° C. | 0 |

EXAMPLE: 4

The process of Example 3 was repeated, but with cetyl trimethyl ammonium chloride in the slow-add. 33 g of cationic surfactant was added to slow addition 1. The emulsion properties were:

| | |
|---|---|
| Solids, % | 50.9 |
| Viscosity (20 rpm, RVT#3) | 54 cps |
| pH | 4.3 |
| % grit (200 mesh) | 0.005 |
| Tg, ° C. | 2 |

EXAMPLE: 5

The emulsion made as in Ex. 3, with the level of cetyl trimethyl ammonium chloride increased to 100 g. The emulsion had the final properties:

| | |
|---|---|
| Solids, % | 52.8 |
| Viscosity (20 rpm, RVT#3) | 75 cps |
| pH | 4.5 |
| % grit (200 mesh) | 0.010 |
| Tg, ° C. | 0 |

EXAMPLE: 6

The emulsion made as in Ex. 3, with butyl acrylate added to the initial monomer; 100 g was added, and the vinyl acetate was reduced to 3100 g. The emulsion results were:

| | |
|---|---|
| Solids, % | 52.7 |
| Viscosity (20 rpm, RVT#3) | 90 cps |
| pH | 4.4 |
| % grit (200 mesh) | 0.016 |
| Tg, ° C. | −3 |

EXAMPLE 7

Ex. 3 with the polyvinyl alcohol changed to a cationic modified PVOH; POVAL CM-318 (Kuraray). It was added at 200 g of a 10% aq. solution in the initial charge.

The emulsion had the final properties:

| | |
|---|---|
| Solids, % | 52.6 |
| Viscosity (20 rpm, RVT#3) | 62 cps |
| pH | 4.5 |
| % grit (200 mesh) | 0.020 |
| Tg, ° C. | 0 |

EXAMPLE 8

The Ex 3 composition was run with the reducing agent changed to ascorbic acid replacing sodium formaldehyde sulfoxylate (SFS). Similar levels were used. Results were as follows:

| | |
|---|---|
| Solids, % | 52.6 |
| Viscosity (20 rpm, RVT#3) | 112 cps |
| pH | 3.75 |
| % grit (200 mesh) | 0.027 |
| Tg, ° C. | +2° C. |

EXAMPLE 9

Ex. 3 with the cationic monomer slow added. 40 g of dimethyl amino ethyl acrylate-methyl chloride quit., 80% solution, added to Slow add 1. The emulsion results were:

| | |
|---|---|
| Solids, % | 50.0 |
| Viscosity (20 rpm, RVT#3) | 344 cps |
| pH | 4.1 |
| % grit (200 mesh) | 0.025 |
| Tg, ° C. | −3° C. |

EXAMPLE 10

A general procedure for the preparation of a vinyl acetate-ethylene copolymer emulsion containing quaternary cationic monomer (dimethyl amino ethyl acrylate-methyl chloride quit. (DMAEA)) is as follows: The initial charge to the reactor includes the following:

| | |
|---|---|
| Water (deionized) | 2100.0 g |
| Ferrous sulfate (1% aq. sol'n) | 16.0 |
| Polyvinyl alcohol (10% aq. Sol'n) | 200.0 |
| Cetyl trimethyl ammonium chloride | 67.0 |
| Ethoxylated alkyl alcohol (10 EO) surfactant | 80.0 |
| Ethoxylated alkyl alcohol (30 EO) surfactant | 120.0 |
| Sodium acetate | 0.5 |
| Versene 100 (1%) | 16.0 |
| DMAEA methyl chloride quat. | 8.0 |
| Phosphoric acid | 1.5 |
| Sodium Form. Sulfoxylate (SFS) | 1.6 |
| Vinyl acetate | 3100.0 |
| Butyl acrylate | 100.0 |

Ethylene—amount to equilibrate reactor to 600 psi at 50° C.

Slow additions:

| | |
|---|---|
| 1. Water | 800.0 |
| Ethoxylated alkyl alcohol (30 EO) surfactant | 40.0 |
| Sodium acetate | 1.2 |
| NMA-LF (48%) | 433.0 |
| 2. Water (deionized) | 250.0 g |
| t-butyl hydroperoxide (70% aq.sol'n) | 16.0 |
| 3. Water (deionized) | 250.0 g |
| Sodium Formaldehyde Sulfoxylate(SFS) | 12.0 |

The pH of the initial aqueous charge was adjusted to 4.0-4.3 with the phosphoric acid. A 10 L stainless steel pressure reactor was filled with initial aqueous mix. It was flushed with nitrogen. With the agitation at about 250 rpm, the vinyl acetate was added. After closing all reactor ports, it was purged twice with nitrogen (25 to 40 psi) and then with ethylene (50 psi). It was then heated to 50° C. Agitation was increased to 550 rpm and it was pressurized with ethylene to 600 psi. The reactor temperature and ethylene pressure were allowed to equilibrate for 15-20 minutes. The ethylene supply was then closed off. Agitation was reduced to 400 rpm.

The reaction was initiated by starting both slow-additions (no. 1 and 2) at 2.5 hr. rates (80 cc/hr). After the initial temperature rise, about 2-5° C., the jacket temperature and oxidizer rate (no. 2) are adjusted to allow the temperature to reach 60° C. in about 15 minutes. The slow addition, no. 1, was started to add uniformly over 4 hrs. During the run, the oxidizer rate is adjusted to maintain a 15-20° C. average temperature delta (reaction temperature minus jacket temperature) The reaction is run until the residual vinyl acetate is reduced to 1.5-2.0% (about 2-2.5 hrs). It is then cooled to 45° C. and transferred to the degassing tank to vent off residual ethylene pressure. Defamer, Colloid 681f (Allied Colloids), was added to the degassing tank followed by finishing redo initiator. This includes 15 g of a 6% t-BHP solution, waiting 5 minutes, then 15 g of a 6% SFS solution added over 15 minutes. This reduces the vinyl acetate to <0.3%. After cooling to 30° C., the pH is adjusted to 4-5 with 14% ammonium hydroxide. The emulsion had the final properties:

| | |
|---|---|
| Solids, % | 52.4 |
| Viscosity (20 rpm, RVT#3) | 156 cps |
| pH | 4.3 |
| % grit (200 mesh) | 0.010 |
| Tg, ° C. | +2° |

EXAMPLE 11

The Ex 10 composition was run using dimethyl amino ethyl methacrylate-methyl chloride quit., (DMAEMA quit) as the quaternary monomer. Results were as follows:

| | |
|---|---|
| Solids, % | 52.2 |
| Viscosity (20 rpm, RVT#3) | 530 cps |
| pH | 4.2 |
| % grit (200 mesh) | 0.010 |
| Tg, ° C. | 0° |

EXAMPLE 12

The Ex 10 composition was run using an amine oxide surfactant as the cationic surfactant instead of cetyl trimethyl ammonium chloride. Results were as follows:

| | |
|---|---|
| Solids, % | 51.5 |
| Viscosity (20 rpm, RVT#3) | 80 cps |
| pH | 4.0 |
| % grit (200 mesh) | 0.008 |
| Tg, ° C. | 0° |

EXAMPLE 13

Ex 10 was run with increased level of DMAEA, methyl chloride quit., 25 g. The results were;

| | |
|---|---|
| Solids, % | 50.0 |
| Viscosity (20 rpm, RVT#3) | 900 cps |
| pH | 4.2 |
| % grit (200 mesh) | 0.025 |
| Tg, ° C. | 0° |

EXAMPLE 14

Ex. 10 was run with the ethylene pressure increased to 650 psi and the vinyl acetate reduced to 3000 g. The emulsion results were:

| | |
|---|---|
| Solids, % | 52.3 |
| Viscosity (20 rpm, RVT#3) | 576 cps |
| pH | 4.1 |
| % grit (200 mesh) | 0.020 |
| Tg, °C. | −12° |

EXAMPLE 15

The Ex. 6 was repeated using NMA-LF (Cytec) at 433 g in slow-add 1. The emulsion results were:

| | |
|---|---|
| Solids, % | 52.1 |
| Viscosity (20 rpm, RVT#3) | 362 cps |
| pH | 4.4 |
| % grit (200 mesh) | 0.015 |
| Tg, °C. | +2° |

EXAMPLE 16

Ex. 10 was repeated at increased NMA level of 520 g. The emulsion results were:

| | |
|---|---|
| Solids, % | 51.1 |
| Viscosity (20 rpm, RVT#3) | 974 cps |
| pH | 4.1 |
| % grit (200 mesh) | 0.006 |
| Tg, °C. | +1° |

EXAMPLE 17

Ex. 10 with the cationic monomer added in the initial charge and slow added. 6 g of DMAEA, methyl chloride quit., 80% solution, added to initial charge and to Slow add 1. The emulsion results were:

| | |
|---|---|
| Solids, % | 53.0 |
| Viscosity (20 rpm, RVT#3) | 750 cps |
| pH | 4.2 |
| % grit (200 mesh) | 0.025 |
| Tg, °C. | −3° C. |

EXAMPLE 18

The emulsion polymers of Examples 3-17 were tested for tensile strength by the procedure of Example 1, and for BZK release by the procedure of Example 2. The results are shown in Table 3.

TABLE 3

| Example # | CD Dry, g/in, Peak Load | CD Wet, g/in. Peak Load | BZK Release, % |
|---|---|---|---|
| 3 | 5849 | 3263 | 51.3 |
| 5 | 5841 | 2981 | 48.7 |
| 6 | 5716 | 3217 | 57.4 |
| 9 | 6302 | 3191 | 58.5 |
| 11 | 5976 | 3313 | 55.5 |
| 13 | 6184 | 3077 | 60.0 |

The data in Table 3 show the utility of the invention in producing good web tensile strength with a high level of BZK release.

What is claimed is:

1. A non-woven product comprising: a) a nonwoven web of fibers; and b) a binder comprising a cross-linkable cationic emulsion copolymer composition at an effective amount to bind the fibers together to form a self-sustaining web, wherein said cationic emulsion copolymer comprises from 0.1 to 25 parts per hundred of cationic monomer units which are polymerized into the backbone of the copolymer; wherein said cationic copolymer comprises a copolymer of vinyl acetate, ethylene, in addition to said cationic monomer units.

2. The non-woven product of claim 1 wherein said product further comprises one or more cationic active ingredients.

3. The non-woven product of claim 1 wherein said emulsion copolymer has a Tg of from −60° C. to +105° C.

4. The non-woven product of claim 3 wherein said emulsion copolymer has a Tg of from −40° C. to +35° C.

5. The non-woven product of claim 1 wherein said product comprises said binder at an add-on level of from 0.1 to 100 percent.

6. The non-woven product of claim 5 wherein said product comprises said binder at an add-on level of from 3 to 30 percent.

7. A non-woven product comprising a) a nonwoven web of fibers; b) a binder comprising a cross-linkable cationic emulsion copolymer composition at an effective amount to bind the fibers together to form a self-sustaining web, wherein the cationic emulsion copolymer comprises from 0.1 to 25 parts per hundred of cationic monomer units which are polymerized into the backbone of the copolymer; and c) one or more cationic active ingredients.

8. The non-woven product of claim 7 wherein said cationic copolymer further comprises vinyl acetate and ethylene monomer units.

9. The non-woven product of claim 7 wherein said cationic copolymer further comprises (meth)acrylate monomer units.

10. The product of claim 7 wherein said composition is free of anionic active ingredients.

11. The product of claim 7 wherein said cationic copolymer emulsion comprises a polymer stabilized with a cationic surfactant or cationic stabilizer.

12. The product of claim 7 comprising from 0.1 to 5 percent by weight of said cationic active ingredient, based on the weight of said binder.

13. The product of claim 12 comprising from 1 to 2 percent by weight of said cationic active ingredient, based on the weight of said binder.

14. The nonwoven product of claim 2, wherein the cationic active ingredient comprises a quaternary alkyl ammonium chloride.

15. The nonwoven product of claim 2, wherein the cationic active ingredient is selected from the group consisting of benzalkonium chlorides, benzethonium chlorides, and combinations thereof.

16. A nonwoven product comprising:
a) a nonwoven web of fibers;
b) a binder comprising a cross-linkable cationic emulsion copolymer composition at an effective amount to bind the fibers together to form a self-sustaining web, wherein said cationic emulsion copolymer comprises from 0.1 to 25 parts per hundred of cationic monomer units which are polymerized into the backbone of the copolymer; and
c) from 0.1 to 5 wt. percent of a cationic active ingredient based on the weight of the binder, which is applied to the nonwoven web.

17. The nonwoven product according to claim 16, wherein the cationic active ingredient is present in an aqueous solution.

* * * * *